US009770041B2

(12) United States Patent
Dong et al.

(10) Patent No.: US 9,770,041 B2
(45) Date of Patent: Sep. 26, 2017

(54) ANTIMICROBIAL WASH

(71) Applicants: Nature Seal Inc., Lincoln, RI (US); The United States of America as Represented by the Secretary of Agriculture, Washington, DC (US)

(72) Inventors: Xiaoling Dong, North Attleboro, MA (US); Joshua Brandt Gurtler, Phoenixville, PA (US); RenSun Lee, North Grafton, MA (US); Stephen A. Santos, Cumberland, RI (US)

(73) Assignees: Mantrose-Haeuser Co., Inc., Westport, CT (US); The United States of America as Represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 14/284,453

(22) Filed: May 22, 2014

(65) Prior Publication Data
US 2014/0348945 A1 Nov. 27, 2014

Related U.S. Application Data

(60) Provisional application No. 61/826,775, filed on May 23, 2013.

(51) Int. Cl.
*A23L 5/00* (2016.01)
*A01N 37/36* (2006.01)
*A01N 37/04* (2006.01)
*A01N 37/02* (2006.01)
*A01N 59/00* (2006.01)
*A23B 7/157* (2006.01)
*A23B 7/10* (2006.01)

(52) U.S. Cl.
CPC ............... *A23B 7/10* (2013.01); *A01N 37/02* (2013.01); *A01N 37/04* (2013.01); *A01N 37/36* (2013.01); *A01N 59/00* (2013.01); *A23B 7/157* (2013.01); *A23L 5/57* (2016.08)

(58) Field of Classification Search
CPC ........ A01N 37/02; A01N 59/00; A01N 37/04; A01N 37/36; A01N 25/02; A23L 1/0011; A23L 5/57; A23B 7/157; A23B 7/10
See application file for complete search history.

(56) References Cited

U.S. PATENT DOCUMENTS

| | | | |
|---|---|---|---|
| 3,364,037 A | 1/1968 | Mink | |
| 5,139,788 A * | 8/1992 | Schmidt | A01N 59/00 424/616 |
| 5,891,392 A * | 4/1999 | Monticello | A01N 59/00 252/186.43 |
| 6,096,348 A | 8/2000 | Miner et al. | |
| 6,207,108 B1 | 3/2001 | Carr et al. | |
| 6,262,038 B1 | 7/2001 | Pierce et al. | |
| 6,348,226 B1 | 2/2002 | McAninch | |
| 6,383,523 B1 | 5/2002 | Murad | |
| 6,479,454 B1 | 11/2002 | Smith et al. | |
| 6,506,417 B1 | 1/2003 | Siddle | |
| 6,627,593 B2 | 9/2003 | Hei et al. | |
| 6,803,066 B2 | 10/2004 | Traeder et al. | |
| 6,964,787 B2 | 11/2005 | Swart et al. | |
| 7,060,301 B2 | 6/2006 | Wei et al. | |
| 7,150,884 B1 | 12/2006 | Hilgren et al. | |
| 8,124,132 B2 | 2/2012 | Hilgren et al. | |
| 8,246,906 B2 | 8/2012 | Hei et al. | |
| 8,263,151 B2 | 9/2012 | Ho | |
| 8,357,413 B2 | 1/2013 | James et al. | |
| 2005/0145825 A1 | 7/2005 | McClung | |
| 2006/0051429 A1 | 3/2006 | Murad | |
| 2009/0192231 A1 | 7/2009 | Lemons | |
| 2009/0324789 A1 * | 12/2009 | Ho | A01N 37/36 426/335 |
| 2010/0055198 A1 * | 3/2010 | Wang | A01N 31/02 424/616 |
| 2011/0172307 A1 * | 7/2011 | Herdt | A01N 37/02 514/558 |
| 2011/0318461 A1 | 12/2011 | Ho | |
| 2013/0065959 A1 | 3/2013 | Ho | |
| 2013/0072563 A1 | 3/2013 | Ho | |
| 2013/0079408 A1 | 3/2013 | Ho | |

FOREIGN PATENT DOCUMENTS

| | | |
|---|---|---|
| CN | 1115601 A | 1/1996 |
| CN | 1705735 A | 12/2005 |
| DE | 29904725 U1 | 8/2000 |
| WO | 9944444 A1 | 9/1999 |

OTHER PUBLICATIONS

Guan CN 111 5601 A Eng. Translation, 1996.*
Ukuku et al. ("Use of hydrogen peroxide in combination with nisin, sodium lactate and citric acid for reducing transfer of bacterial pathogens from whole melon surfaces to fresh-cut pieces," in International Journal of Food Microbiology 104 (2005) 225-233).*
Martin and Maris, "Synergism between hydrogen peroxide and seventeen acids against five agri-food-borne fungi and one yeast strain," in Journal of Applied Microbiology, pp. 1451-1460.*
Martin and Maris, ("Synergism between hydrogen peroxide and seventeen acids against six bacterial strains," in Journal of Applied Microbiology, 113, 578-590, 2012).*
Ukuku, ("Effect of sanitizing treatments on removal of bacteria from cantaloupe surface, and re-contamination with *Salmonella*," in Food Microbiology 23 (2006) 289-293).*
Ukuku, ("Effect of hydrogen peroxide treatment on microbial quality and appearance of whole and fresh-cut melons contaminated with *Salmonella* spp." in International Journal of Food Microbiology 95 (2004) 137-146).*

(Continued)

*Primary Examiner* — Blessing M Fubara
(74) *Attorney, Agent, or Firm* — Calfee, Halter & Griswold LLP

(57) ABSTRACT

A new antimicrobial wash for treating fresh fruits and vegetables to reduce microorganisms, especially human pathogens, comprises an aqueous solution of hydrogen peroxide and one or more fruit acids.

13 Claims, No Drawings

(56) References Cited

OTHER PUBLICATIONS

Website printout; Peracetic acid-Wikipedia, the free encyclopedia; http://en.wikipeida.org/wiki/Peracetic_acid, printed May 3, 2013, 2 pages.

Islam, Mominul, "Liquid Chromatographic Separation and Simultaneous Analyses of Peroxycitric Acid and Citric Acid Coexisting with Hydrogen Peroxide in the Equilibrium Mixture," Oxford Journals, Mathematics & Physical Sciences, Journal of Chromatographic Science, vol. 49, Issue 1, pp. 40-45.

Search Report for European Patent Application No. EP 1480-965 dated Dec. 2, 2016.

First Office Action for Chinese Patent Application No. 21480029782.X dated Jul. 4, 2017.

* cited by examiner

ANTIMICROBIAL WASH

CROSS-REFERENCE TO RELATED APPLICATION

This application is based on and claims priority to prior U.S. Provisional Application Ser. No. 61/826,775, filed May 23, 2013, the disclosure of which is incorporated herein by reference.

SUMMARY AND DETAILED DESCRIPTION

A new antimicrobial wash for treating fresh fruits and vegetables, both whole and cut, (collectively "produce") to reduce microorganisms, especially human pathogens, comprises an aqueous solution of hydrogen peroxide and one or more fruit acids. In this context, "solution" will be understood to mean a true solution, i.e., a composition in which all of the indicated ingredients other than water are dissolved in the aqueous phase. Thus, "solution" excludes dispersions in which an indicated ingredient is present in a greater than saturation concentration whereby at least some of this ingredient is present as a dispersed solid.

Suitable fruit acids for this purpose include malic acid (including DL-Malic acid, L-malic acid and mixtures thereof), citric acid, tartaric acid, mandelic acid and mixtures thereof. Malic acid, citric acid, tartaric acid and mixtures thereof are preferred.

In a preferred embodiment, lactic acid is included in the inventive antimicrobial wash, as even better results can be achieved if lactic acid is present.

The concentrations of ingredients in the inventive antimicrobial wash when in a use form, i.e., when applied to the produce, are set forth in the following Tables 1 and 2:

TABLE 1

Dilute (Use) Form
Ingredient Concentrations (wt. %) and Weight Ratios
Lactic Acid Absent

|  | Broadest | Broad | Intermediate | Narrow |
| --- | --- | --- | --- | --- |
| $H_2O_2$ | 0.01-0.45% | 0.02-0.20% | 0.025-0.15% | 0.025-0.10% |
| fruit acid | 0.025-1.0% | 0.05-1.0% | 0.10-0.8% | 0.2-0.6% |

The ratio of $H_2O_2$ to fruit acid ("$H_2O_2$/fruit acid ratio") in these aqueous antimicrobial washes can vary widely. For example, this ratio can be as low as 0.01 to as high as 10. More commonly, the $H_2O_2$/fruit acid ratio will be 0.02-4.0, or even 0.03-1.5. If desired, the $H_2O_2$/fruit acid ratio can be 0.04-0.5, 0.07-0.4 or even 0.1-0.36.

TABLE 2

Dilute (Use) Form
Ingredient Concentrations (wt. %) and Weight Ratios
Lactic Acid Present

|  | Broadest | Broad | Intermediate | Narrow |
| --- | --- | --- | --- | --- |
| $H_2O_2$ | 0.01-0.25% | 0.02-0.20% | 0.025-0.15% | 0.025-0.10% |
| fruit acid | 0.025-1.0% | 0.05-1.0% | 0.10-0.8% | 0.2-0.6% |
| lactic acid | 0.005-0.20% | 0.005-0.15% | 0.01-0.1% | 0.02-0.05% |
| fruit acid + lactic acid | 0.03-1.2% | 0.055-1.15% | 0.10-0.90% | 0.20-0.65% |

The ratio of lactic acid to fruit acid ("lactic acid/fruit acid ratio") in these aqueous antimicrobial washes can vary widely. For example, this ratio can be as low as 0.005 to as high as 8. More commonly, the lactic acid/fruit acid ratio will be 0.006-3.0, 0.01-3.0, 0.02-2.0, 0.03-1.0, or even 0.033-0.25.

Similarly, the ratio of $H_2O_2$ to fruit acid ("$H_2O_2$/fruit acid ratio") in these aqueous antimicrobial washes can also vary widely. For example, this ratio can be as low as 0.01 to as high as 10. More commonly, the $H_2O_2$/fruit acid ratio will be 0.02-4.0, 0.03-1.5, 0.04-1.0, or even 0.1-0.5.

In addition, the ratio of $H_2O_2$ to lactic acid ("$H_2O_2$/lactic acid ratio") in these aqueous antimicrobial washes can also vary widely. For example, this ratio can be as low as 0.05 to as high as 50. More commonly, the $H_2O_2$/lactic acid ratio will be 0.1-40, 0.2-30, 0.3-10, 0.4-7.5, 0.5-5.0, or even 1.0-3.0

Normally, the inventive antimicrobial wash, when in a use concentration, will have a pH of about 2.0 to 4.0, more typically about 2.4 to 3.5, or even about 2.5 to 3.3.

The inventive antimicrobial wash is desirably free or essentially free of ingredients found in earlier antimicrobial compositions. Examples include peroxyacetic acid, surfactants, carboxylic acid esters and other solvents in addition to water. In particular, the inventive antimicrobial wash is free of alcohols, both monohydric and polyhydric, as well as other oxygenated organic solvents.

In some embodiments, the inventive microbial wash is also free, or essentially free, of salts and other ingredients capable of releasing a cation in aqueous solution. In other embodiments, calcium and/or magnesium salts can be included in the inventive antimicrobial wash. If so, the combined concentration of these calcium and magnesium salts will typically be on the order of about 0.001 to 0.05 wt %, more typically about 0.005 to 0.02 wt %.

The inventive antimicrobial wash can be manufactured and shipped in concentrated form and then diluted with water immediately before use. For example, a concentrate containing all of the ingredients of the inventive antimicrobial wash to be made, in the same relative proportions as this antimicrobial wash, can be made up in bulk, packaged in suitable containers, stored, shipped, and then diluted with a suitable amount of water immediately before use. The amount of hydrogen peroxide in such concentrates can be as little as 1 wt. % and as much as 35 wt. %, but will typically be on the order of 1-25 wt. %, 2-25 wt. %, 2 to 15 wt. %, 3.5-20 wt. % or even 3.5 to 10 wt. %.

Any suitable application technique can be used for applying the inventive antimicrobial wash to produce including spraying (e.g., direct spraying, misting, fogging, etc.), curtain coating, and the like. Immersion coating has been found especially useful. Regardless of the particular application technique used, the contact time during which the inventive antimicrobial wash remains in contact with the produce being treated is desirably about 1 to 10 minutes, preferably about 2 to 5 minutes.

Thus, in this document, we disclose processes for treating fresh fruits and vegetables to reduce microbial contamination of the surface of the fresh fruit or vegetable being treated, this process comprising contacting the surface of the fresh fruit or vegetable with an antimicrobial wash comprising an aqueous solution containing a sufficient amount of hydrogen peroxide and one or more fruit acids to reduce microbe contamination of the surface of the produce being treated (a "microbe-reducing effective amount"). The terms "treatment" and "treating" as used herein will therefore be understood to cover any treatment that reduces microbial contamination of the surface of fresh fruits or vegetables.

In this connection, it will be appreciated that the application techniques typically used for applying antimicrobial washes to fresh fruits and/or vegetables (e.g., direct spraying, misting, fogging, curtain coating, immersion, etc.) normally recycle the antimicrobial wash for reuse on many subsequent batches of fresh fruits and/or vegetables. Water washing fresh produce is normally sufficient to remove microorganisms and pathogens from produce surfaces, even if the wash water contains no special antimicrobial agents. The problem arises, however, when this wash water is reused. This is because the microbes removed from fruit or vegetables remain in this wash water where they rapidly increase and then contaminate the second and subsequent fruit or vegetables treated with the same wash water. So, in order for an antimicrobial wash to be effective in such processes in terms of reducing microbial contamination of multiple batches of fresh fruit or vegetables, the antimicrobial wash needs to contain enough antimicrobial agents to reduce the microbial contamination of this wash water over time. So, in the context of this disclosure, a "microbe-reducing effective amount" of hydrogen peroxide and one or more fruit acids will be understood to mean amounts which are sufficient to reduce microbial contamination of this wash water relative to wash water not containing any antimicrobial agents. In general, it is desirable to select concentrations of fruit acids, hydrogen peroxide and lactic acid in the ranges set forth in the above Tables 1 and 2. However, exact concentrations can be determined by one of ordinary skill in the art by routine experimentation.

Preferably, the amount of inventive aqueous antimicrobial wash used as well as the concentrations of its active ingredients will be selected so as to avoid causing damage to the fresh fruits or vegetables being treated. Of course, the precise amount needed will vary in accordance with the particular compound or composition used, the fresh fruits or vegetables to be treated, and the environment in which the fresh fruits or vegetables are located. The precise amount of the compound or composition can easily be determined by one skilled in the art given the teaching of this document. For example, one skilled in the art could follow the procedures utilized herein to determine the amount of inventive aqueous antimicrobial wash to use as well as the concentrations of active ingredients therein so as to achieve a statistically significant reduction in microbial contamination in comparison to a negative control.

Also, it should be understood that other compounds may be added to the inventive aqueous antimicrobial wash provided they do not substantially interfere with its intended activity and efficacy. To this end, whether or not such another compound might interfere with the activity and/or efficacy of the inventive aqueous antimicrobial wash can be determined, for example, by the procedures utilized herein.

After treatment is completed, any residual antimicrobial wash still remaining on the produce can be removed by rinsing with potable water, if desired.

After treatment and any optional rinsing step are completed, the treated produce can be used in any conventional way. For example, the treated produce (both whole and cut) can be packaged, stored and shipped in accordance with normal practice. If so, the packaged produce is desirably stored at 15 to 25° C., preferably 10 to 15° C., 5 to 10° C., or even 2 to 5° C. Alternatively, the treated produce can be frozen or dried in a conventional way.

Finally, the treated produce can also be treated in a conventional way with an antioxidant solution to prevent enzymatic discoloration before packaging. If so, the produce may optionally be rinsed with potable water to remove any residual antimicrobial wash that may be remaining on the treated produce.

EXAMPLES

In order to more thoroughly describe this invention, the following working examples are provided.

Examples 1 and 2 and Comparative Examples A and B

Bay spinach leaves were separated into groups weighing 8 g per group, after which each group was placed on the top of a surface-sanitized test tube rack under a laminar flow hood. Each spinach leaf was then exposed to UV light for 5 min to decrease its concentration of surface microbes. After 5 min, each leaf was carefully turned over using tongs or ethanol-sanitized nitrile gloves and the other side of the leaf then exposed to UV light for an additional 5 min.

Each decontaminated bay spinach leaf was then inoculated with certain human pathogens, in particular *E. coli* 0157:H7, *Listeria monocytogenes* and *Salmonella* serotypes, by flooding each set of leaves in an inoculum of the pathogen for 30 sec. The excess inoculum was then shaken off with tongs, after which the leaves were air dried on the top of their test tube racks in a laminar flow hood for 1 hour. Then each sample was added to 500 ml of an antimicrobial wash treatment solution in a 1 or 2 liter beaker, after which the contents of each beaker were stirred with a sterile pipette or stir bar for 5 minutes. The treated leaves were then removed from their antimicrobial wash solution, shaken to remove excess liquid, and then added to 32 ml of DE (Dey-Engley) neutralizing broth in a sterile/filtered/80 ml stomacher bag. The leaves were then pummeled in the mini-stomacher for 3 min, and contents of each bag then filtered to recover the supernatant liquid. The supernatant was then used to make serial dilutions which were plated onto Tryptic Soy Agar+0.1% sodium pyruvate+100 ppm nalidixic acid and incubated for 24 h at 37° C. Survival pathogens in the antimicrobial wash water after treatment were also plated out. Cfu (colony forming units) were manually counted or counted by a colony counter.

The counts obtained from each sample were then compared with a positive control in which the inoculated leaves were washed with 0.1 wt. % peptone water in place of antimicrobial solutions (as Example B in Table 3).

The counts obtained from each sample were then compared with a positive control in which the inoculated leaves were added directly to the DE neutralizing broth without being contacted with an antimicrobial treatment solution first, Four different aqueous antimicrobial wash solutions were tested, the compositions of which are set forth in the following Table 3:

TABLE 3

Chemical Compositions of Aqueous Antimicrobial Washes

| Example | Composition |
|---|---|
| A | 20 ppm peroxyacetic acid |
| 1 | 0.344 wt. % malic acid, 0.051 wt. % lactic acid, 0.104 wt. % $H_2O_2$ |
| 2 | 0.462 wt. % malic acid, 0.068 wt. % lactic acid, 0.14 wt. % $H_2O_2$ |
| B | 0.1 wt. % peptone water |

The results obtained are set forth in the following Tables 4, 5 and 6:

TABLE 4

Antimicrobial Wash Reduction of *E. coli* 0157:H7 from baby Spinach

| Example | Log reduction of *E. coli* 0157:H7 from baby spinach/5 minutes | Population of 0157:H7 (log) in antimicrobial wash water |
|---|---|---|
| A | 0.53 | 0.00 |
| 1 | 1.16 | 0.00 |
| 2 | 1.58 | 0.00 |
| B | 0.77 | 3.77 |

Baby Spinach was inoculated to 6.72 log CFU/g of *E. coli* 0157:H7 before antimicrobial solution wash

TABLE 5

Antimicrobial Wash Reduction of *Salmonella* from baby spinach (Four *Salmonella* strains: Stanley, Montevideo, St. Paul and Newport)

| Example | Log reduction of *Salmonella* from baby spinach/5 minutes | Population of *Salmonella* (log) in antimicrobial wash solution |
|---|---|---|
| A | 0.78 | 0.00 |
| 1 | 1.18 | 0.00 |
| 2 | 1.35 | 0.00 |
| Sterile deionized water | 0.78 | 1.73 |

Baby Spinach was inoculated to 7.43 log CFU/g of *Salmonella* four strains: Stanley, Montevideo, St. Paul and Newport

TABLE 6

Antimicrobial Wash Reduction of *Listeria monocytogenes* from baby spinach Five strains, L2624 (CDC 2001 cantaloupe outbreak strain, serotype 1/2b), L2625 (CDC 2011 cantaloupe outbreak strain, serotype 1/2a - different molecule type than L2624), L008 (Canadian cole slaw/cabbage epidemic outbreak, serotype 4b), L499 (Historic U.S. outbreak strain human isolate, serotype 1/2a), L502 (Historic 1994 Illinois foodborne outbreak serotype 1/2b)"

| Antimicrobial Wash | Log reduction of *L. monocytogenes* from baby spinach/5 minutes | Population of *L. monocytogenes* (log) in antimicrobial wash water |
|---|---|---|
| A | 0.91 | 0.00 |
| 1 | 1.09 | 0.00 |
| 2 | 0.93 | 0.00 |
| B | 0.40 | 2.59 |

Baby Spinach was inoculated to 8.00 log CFU/g of *L. monocytogenes*

As can be seen from the above examples, the inventive aqueous antimicrobial wash is considerably more effective than conventional antimicrobial compositions in terms of reducing microbial contamination of the fresh vegetable being treated.

After the above treatments had been completed, the wash waters used in each example were also analyzed for pathogens. It was found that the wash water used in Examples 1 and 2 representing this invention contained no pathogen accumulation. In contrast, the wash water used in Comparative Example B (0.1 wt. % peptone water) contained 3.77 log *E. coli* O157, 1.73 log *Salmonella* and 2.59 log *L. monocytogenes* accumulations after a single wash of inoculated baby spinach.

Example 3-9

In this example, the general method of BS EN 1276 was used to assess the effectiveness of seven additional aqueous antimicrobial wash compositions of this invention in connection with reducing microbial contamination of the wash water used for treating fresh fruits and vegetables. The make-up of these seven additional aqueous antimicrobial wash compositions was generally the same as those of the above Examples 1 and 2, although the total concentration of active ingredients in these compositions varied from most concentrated (Example 3) to least concentrated (Example 9). The microorganism used in this test was *E. coli* O157, the interfering substance was bovine albumin and the contact time was 5 minutes.

A standard test suspension containing microorganism cells at a concentration of 8.0-9.0 log/ml was prepared as an inoculum. One ml of the interference substance was pipetted into a sterile 14 ml test tube, followed by 1 ml of the microorganism test suspension and mixed well. After 2 minutes, 8 ml of the aqueous antimicrobial wash being tested was added and vortexed to mix. After a contact time of 5 minutes, 1 ml of the aliquot was transferred to a sterile 14 ml test tube, which was neutralized by diluting to a DE-neutralizing broth. The composition was then plated onto Tryptic Soy Agar+0.1% sodium. After incubating 24 hrs at 37° C., the colony forming units were counted manually (only colonies with 25-250/plate were counted), and the concentration of microbes in terms of CFU/ml was then calculated using the formula CFU/ml=colonies counts× dilution factor.

Two different interference substances were used. The first interference simulating "dirty conditions" contained 3 g of bovine albumin/100 ml. One ml of this interference was pipetted into the test tube, followed by adding 1 ml of the microbial suspension. The final concentration of bovine albumin in this test tube was 0.3%, thereby simulation dirty condition.

The second interference simulating "clean conditions" contained 0.3 g bovine albumin/100 ml. One ml of this interference was pipetted into the test tube, followed by adding 1 ml of the microbial suspension. The final concentration of bovine albumin in this test tube was 0.03%, thereby simulation clean conditions.

The results obtained are set forth in the following Table 7:

TABLE 7

*E. coli* O157 Inactivation under both "DIRTY" & "CEALN" conditions per BS EN method (2009)

| Examples | *E. coli* Log Reduction CLEAN condition/5 minutes contact time | *E. coli* Log Reduction DIRTY condition/5 minutes contact time |
|---|---|---|
| 3 | ≥6.9 | ≥6.9 |
| 4 | ≥6.9 | ≥6.9 |
| 5 | ≥6.9 | ≥6.9 |
| 6 | ≥6.9 | ≥6.9 |
| 7 | ≥6.9 | ≥6.9 |
| 8 | 7.3 | ≥6.9 |
| 9 | 7.2 | 3.84 |

As can be seen from this table, except for the most dilute composition, Example 9, all of these inventive aqueous antimicrobial washes achieved a reduction in *E. coli* concentration of at least log 6.9 when tested under both the "clean" and "dirty" conditions of this test. Moreover, even the most dilute of these composition, Example 9, achieved a reduction in *E. coli* concentration of at least log 6.9 when tested under the "clean" conditions of this test. This clearly demonstrates that the inventive antimicrobial washes will be highly effective in terms of reducing the microbial contamination of wash water which is recycled for reuse in connection with the antimicrobial treatment of multiple batches fresh fruits and vegetables.

Although only a few embodiments of this invention have been described above, it should be appreciated that many modifications can be made without departing from the spirit and scope of this invention. All such modifications are intended to be included within the scope of this invention, which is to be limited only by the following claims:

The invention claimed is:

1. An antimicrobial wash consisting of water, hydrogen peroxide, one or more fruit acids and lactic acid.

2. The antimicrobial wash of claim 1, wherein the fruit acid is one or more of malic acid, citric acid, tartaric acid and mandelic acid.

3. The antimicrobial wash of claim 2, wherein the fruit acid is citric acid.

4. The antimicrobial wash of claim 2, wherein the antimicrobial wash consists of water, 0.02-0.20% $H_2O_2$, 0.05-1.0 wt. % fruit acid and 0.005-0.15 wt. % lactic acid, and further wherein the lactic acid/fruit acid ratio in the antimicrobial wash is 0.02-2.0, the $H_2O_2$/fruit acid ratio in the antimicrobial wash is 0.04-1.0, and the $H_2O_2$/lactic acid ratio in the antimicrobial wash is 0.4-7.5.

5. The antimicrobial wash of claim 4, wherein the fruit acid is citric acid.

6. A process for treating a fresh fruit or vegetable to reduce microbial contamination of the surface of the fresh fruit or vegetable, the process comprising contacting the surface of the fresh fruit or vegetable with an antimicrobial wash consisting of water, hydrogen peroxide, one or more fruit acids and lactic acid.

7. The process of claim 6, wherein the process is carried out on multiple batches of fresh fruit and/or fresh vegetables, and further wherein the antimicrobial wash used to treat at least one of these batches is recycled for reuse in treating at least another of these batches.

8. The process of claim 6, wherein the fruit acid is one or more of malic acid, citric acid, tartaric acid and mandelic acid.

9. The process of claim 8, wherein the fruit acid is citric acid.

10. The process of claim 6, wherein the antimicrobial wash consists of water, 0.02-0.20% $H_2O_2$, 0.05-1.0 wt. % fruit acid and 0.005-0.15 wt. % lactic acid, and further wherein the lactic acid/fruit acid ratio in the antimicrobial wash is 0.02-2.0, the $H_2O_2$/fruit acid ratio in the antimicrobial wash is 0.04-1.0, and the $H_2O_2$/lactic acid ratio in the antimicrobial wash is 0.4-7.5.

11. The process of claim 10, wherein the fruit acid is citric acid.

12. An antimicrobial wash consisting of water, 1-35 wt. % hydrogen peroxide, one or more fruit acids in an amount such that the $H_2O_2$/fruit acid ratio in this antimicrobial wash is 0.02-4.0, and lactic acid in an amount such that the $H_2O_2$/lactic acid ratio in this antimicrobial wash is 0.1-40.

13. The antimicrobial wash of claim 12, wherein the fruit acid is citric acid.

* * * * *